(12) United States Patent
Ding et al.

(10) Patent No.: US 6,453,192 B1
(45) Date of Patent: Sep. 17, 2002

(54) DETECTION OF VENTRICULAR ECTOPIC BEATS USING VENTRICULAR ELECTROGRAM

(75) Inventors: Jiang Ding, Maplewood; Julio C. Spinelli, Shoreview; Yinghong Yu, Maplewood, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/523,616

(22) Filed: Mar. 13, 2000

(51) Int. Cl.[7] .............................................. A61B 5/0452
(52) U.S. Cl. ........................................ 600/516; 607/24
(58) Field of Search ............................. 600/516; 607/25

(56) References Cited

U.S. PATENT DOCUMENTS

| | | | | |
|---|---|---|---|---|
| 4,115,864 A | * | 9/1978 | Vick et al. ................... | 714/815 |
| 5,058,599 A | * | 10/1991 | Andersen ..................... | 600/518 |
| 5,603,331 A | * | 2/1997 | Heemels et al. ............. | 600/508 |
| 6,026,320 A | * | 2/2000 | Carlson et al. .............. | 500/510 |

* cited by examiner

*Primary Examiner*—Carl H. Layno
(74) *Attorney, Agent, or Firm*—Nikolai & Mersereau, P.A.; Thomas J. Nikolai

(57) ABSTRACT

A method of accurately determining if ectopic beats are occurring in the heart by detecting the time interval, T, between a point $Q^*$ defined is the onset of the QRS complex and the peak value of R ($T=Q^*R$) during a heart beat cycle and comparing that time with a running mean value calculated from normal heartbeats. A beat is identified as an ectopic beat if the $Q^*R$ time interval for a current beat is at least four standard deviations from the mean $Q^*R$ time interval of normal preceding beats. The electrodes for detecting the ectopic beats may be inside the patient's heart or on the patient's skin. If more than one electrode is used for monitoring the depolarization of the heart, then by combining the $Q^*R$ intervals (e.g. using a triangulation method) calculated from different electrodes, the location of the ectopic excitation can be determined and identified. The method of determining and localizing ectopic beats may be used in a pacing device to initiate ectopic beat handling procedures and to analyze the nature and possible trend of ectopic activities. This method of using the $Q^*R$ interval is independent of the PR or RR intervals normally measured and used to detect early ectopic beats and is therefore a more accurate method, since ectopic beats may occur at any time independent of PR or RR intervals.

30 Claims, 2 Drawing Sheets

DETECTION OF VENTRICULAR ECTOPIC BEATS USING VENTRICULAR ELECTROGRAM

BACKGROUND OF THE INVENTION

I. Field of the Invention

This invention relates to detection of ectopic beats in the heart by analyzing Q*R time intervals on cardiac electrograms.

II. Description of the Related Art

Time-domain analysis has been widely used to detect premature ventricular contraction (PVC) caused by an ectopic beat. This analysis is based on the relationship between sensed atrial depolarization P and/or ventricular depolarization R. For example, a sensed ventricular beat R without a preceding sensed atrial beat P is considered a PVC. Other examples of PVCs are, a ventricular beat R that is sensed very shortly after sensing atrial activity P or a sensed ventricular beat R with a sudden shortening ventricular beat interval.

Although time-domain analysis with the timing of ventricular beats R and atrial beats P is simple and easy to use, it has limited applications. For example, it can only detect ectopic beats that occur significantly earlier than beats in normal cycles. Yet a ventricular ectopic beat can occur at any time, regardless of the preceding atrial or ventricular events. An ectopic beat can occur after a sensed atrial beat without a very-short PR or RR interval and is thus mistakenly interpreted as a normal beat. Similarly, a post ventricular atrial refractory period (PVARP) of an implanted pacemaker that is triggered by an ectopic beat could mask the pacemaker's detection of the next P-wave, making the system falsely double-count PVCs.

Morphology analysis has also been employed instead of time-domain analysis because ventricular ectopic beats tend to have different shapes in electric response signal than normal ventricular beats or super-ventricular ectopic beats. Yet, such analysis is much more complicated than the time domain analysis.

Furthermore, the prior art methods of detecting ectopic beats using either external ECG equipment or implanted dual chamber pacemakers or pacemaker/defibrillators cannot accurately pinpoint the source of the ectopic beats. Such information may be useful in treating patients with arrhythmia.

SUMMARY OF THE INVENTION

In implementing the present invention, a cardiac rhythm management device is programmed to measure the time interval between the earliest activation of the ventricular polarization, referred to herein as Q*, and the peak of the following ventricular depolarization signal, R. The measured interval is referred to as T and is equal to the time between the Q* point on the QRS complex and R or T=Q*R. The mean value of T and standard deviation are calculated dynamically on a beat-to-beat basis from normal heartbeats for the patient being monitored. It has been empirically determined that any T values of a given beat greater than about 4 standard deviations of the mean T value is considered to be associated with an ectopic beat.

The algorithm for measuring for ectopic beats described herein have several advantages over known prior art methods. Prior art methods have used the PR interval or the RR interval to determine if an ectopic beat has occurred. But, as mentioned above, ectopic beats occur independently of the PR or RR intervals, making these prior art methods unreliable indicators of ectopic beats.

Another advantage of using the T=Q*R interval method of the present invention is that if more than one electrode is used, the location or origin of ectopic excitation can be estimated.

The Q*R method described herein is based somewhat on morphology rather than purely on timing since the ectopic beat can originate from anywhere at any time. Therefore the Q*R method combines the advantages of timing and morphology methods to improve the detection of ectopic beats.

More accurate diagnosis of arrhythmias and better performance of pacemakers incorporating the ectopic beat detection algorithm of the present invention can result from a utilization of this invention.

OBJECTS OF THE INVENTION

It is a principal object of the invention to providing an algorithm for a microprocessor-based cardiac rhythm management device that accurately detects the occurrence of ectopic beats in the heart.

It is a further object of the invention to provide a simpler method for detecting ectopic beats in the heart than used in prior art systems.

Another object of the invention is to provide an ectopic beat detector utilizing only one ventricle sensor and no atrial sensor.

It is an object of the invention to provide an ectopic beat sensing algorithm that is capable of detecting where an ectopic beat originates within the heart.

Other objects, advantages and novel features of the present invention will become apparent from the following detailed description of the invention when considered in conjunction with the accompanying drawings

DESCRIPTION OF THE PREFERRED EMBODIMENTS

A ventricular ectopic beat is a heartbeat triggered at a point on a ventricle other than due to normal propagation of a depolarization wave from the sinus node and atrioventricular node to ventricular tissue via the His bundle. Such beats are abnormal and may lead to more severe arrhythmia such as ventricular tachycardia or fibrillation. It is important to diagnose such ectopic beats, and it is also useful to locate where they originate because this information may lead to possible treatment of the heart conditions that cause the ectopic beats. For patients with pacemakers, the pacemaker may be set to appropriate handling options for this abnormality.

Figure 1:
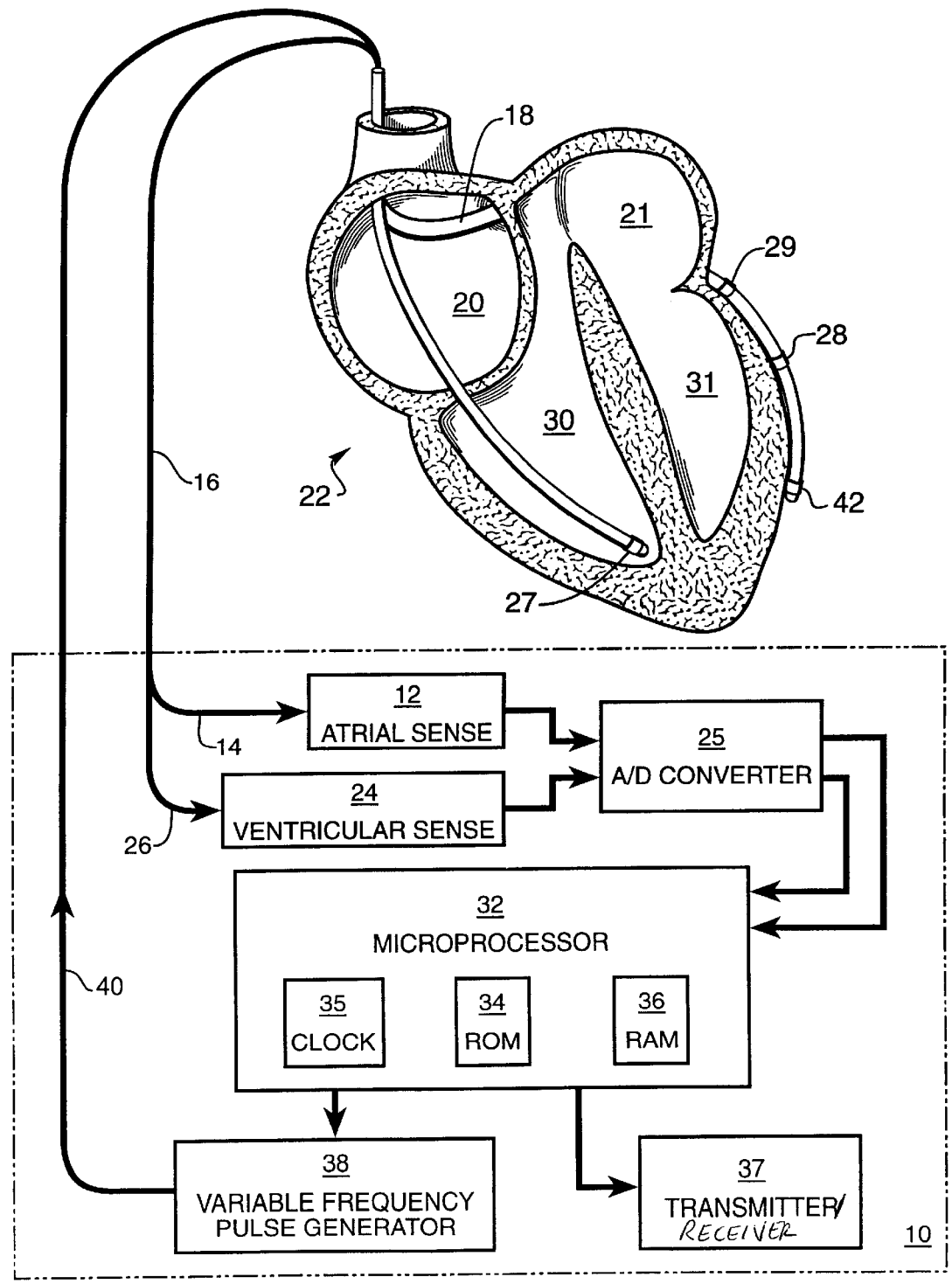
FIG. 1 is a block diagram of a cardiac rhythm management device incorporating the Ventricular Ectopic Beat Detection apparatus and method of the present invention.

FIG. 1 shows a cardiac stimulating device 10 connected to a heart 22 having a right atrium 20 a left atrium 21 a right ventricle 30 and a left ventricle 31. Sensing electrode 28 on a lead 18 is disposed on the myocardium of the left ventricle 31, or as shown in FIG. 1, on the epicardium. A cardiac stimulating electrode 42 is similarly attached. Sensing electrode 28 on lead 18 has a conductor 16 connecting sensing electrode 28 to the ventricular sense amplifier 24 in the stimulating device 10. The analog signals from the ventricular sense amplifier 24 then go to A/D converter 25. The digital signals from the A/D converter 25 are then stored in RAM 36 of microprocessor 32. The microprocessor 32 has a clock 35 for timing events, such as when signals are received, and: storing that information in RAM 36. The ROM 34 in microprocessor 32 contains a program for determining values for Q*, R, and calculating the Q*R interval, providing smoothing by means of a moving average windows for Q*R, calculating the mean Q*R interval, the mean square error of Q*R, and the standard deviation of Q*R. The pacing device 10 may have a telemetry unit 37 to transmit and receive data from a programmer or monitor located outside of the body. The pacing device 10 also has a variable frequency pulse generator 38 controlled by the microprocessor 32 and connected by conductor 40 in lead 18 to cardiac stimulating electrode 42 to pace the heart 22.

The minimum requirement for detection of ectopic beats is to have one ventricular electrode (e.g. electrode 28), placed either endocardially or epicardially on one ventricle (e.g. left ventricle 31), an amplifier 24 for receiving signals from the ventricular electrode 28, an analog-to-digital converter (A/D) 25, a microprocessor 32 having a RAM 36 and a ROM 34 and a special real-time data processing software in the microprocessor 32. The electrode 28 can be a standard unipolar or bipolar sensing electrode. The electrode 28 is used to detect ventricular depolarization events. The amplifier 24 for the ventricular sense electrode 28 should be wide band (e.g. 14–70 Hz in bandwidth), so that both near-field and far-field ventricular electric activities can be detected. Electrical signals associated with activities in the systolic phase of one cardiac cycle (beat) are referred to here as a QRS complex. The A/D converter 25, having a sampling rate of 250 Hz or higher, is used to digitize the analog signals from the amplifier 24 and store the data in RAM 36. Software stored in ROM 36 is used in microprocessor 32 to process and analyze the amplified ventricular electrical signals, search for ectopic beats and display the results. The algorithms employed in this software are diagrammed in FIG. 2 and described below.

Figure 3:
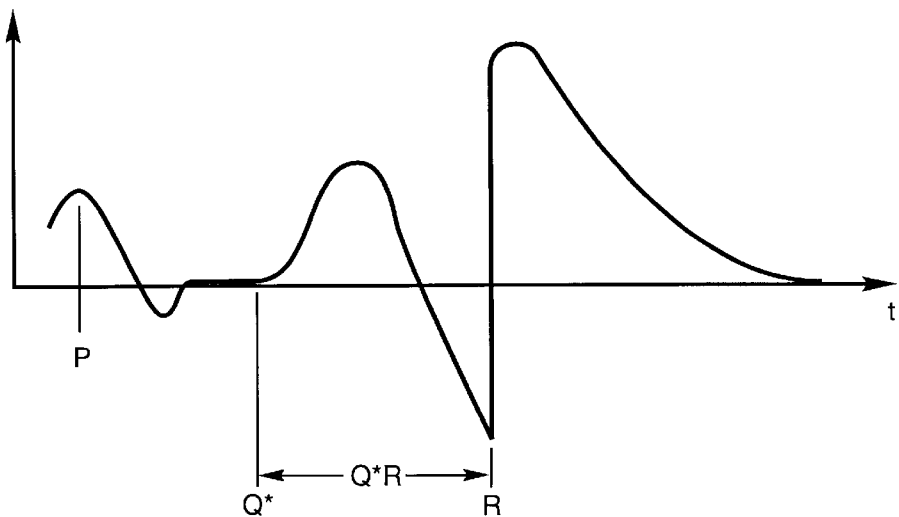
FIG. 3 is an electrogram waveform illustrating the Q*R intervals.

The digitized data in RAM 36 is first signal processed by being smoothed by a weighted N-point moving window 50. Then a time interval, T, between two fiducial points, Q* and R, in a QRS complex is calculated (block 51) wherein T=Q*R. Here R is the largest peak of the QRS complex and Q* is defined as the point at which the absolute slope is 2% of the maximum absolute slope prior to the largest peak R as shown in FIG. 3. Although Q*, as used herein, is the point on the QRS complex where the absolute slope is 2% of the maximum absolute slope prior to the largest peak, other values for Q* may be used.

Figure 2:
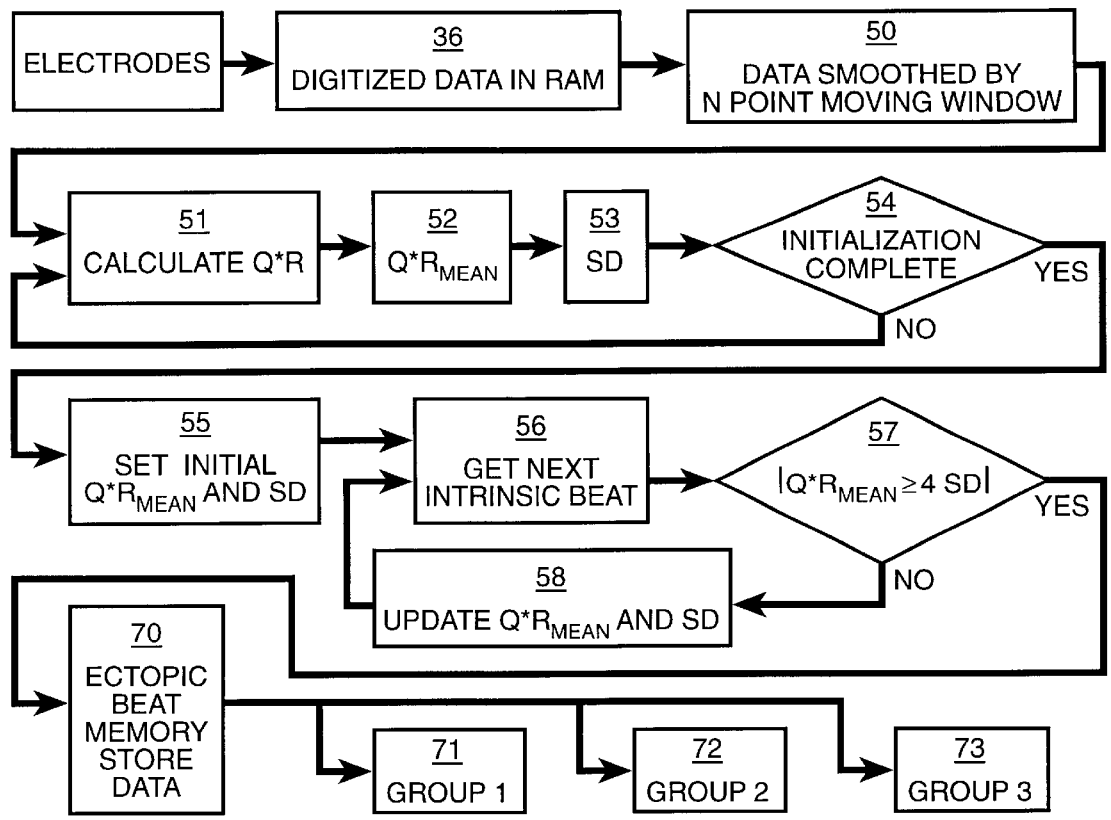
FIG. 2 is a flow diagram illustrating the algorithm for implementing the invention.

Before comparisons can be made of a current heartbeat to the running mean and standard deviations of Q*R to check for ectopic beats, an initialization of data is collected to compare beats as indicated by block 54 in FIG. 2.

At the beginning of the process the Q*R values 51 are calculated on a beat-by-beat basis. The mean Q*R values are computed (block 52) and the standard deviation (SD) is calculated (block 53) and updated dynamically from normal beats. During the initialization step 54, data from a total of M normal beats are collected (under manual observation and intervention). The Q*R values calculated at block 51 are calculated from these collected normal beats and averaged, using standard method, to obtain the initial Q*R mean and the SD to be used for comparison with subsequent beats. For each new or current intrinsic beat, a comparison is made at decision block 57 to determine if its Q*R value is within 4 SDs of the previous mean. If the beat is less than 4 SDs, then the beat is considered a normal beat and the previous mean and the SD are updated at block 58 using the following formula:

$$Mean_i = k1 \times Mean_{i-1} + k2 \times Q^*R_i$$

$$MSE_i = k1 \times MSE_{i-1} + k2 \times (Q^*R_i - Mean_i)^2$$

$$SD_i = \sqrt{MSE_i}$$

where $Mean_{i-1}$ and $MSE_{i-1}$ are the mean and mean square error for the previous beat; $Q^*R_i$ is the Q*R value from the current beat; $Mean_i$, $MSE_i$ and $SD_i$ are the updated mean, mean square error, and standard deviation, respectively; k1, k2 are weighting coefficients. In one example, k1=(M−1)/M, and k2=1/M.

If the Q*R value from a current beat at block 56 is at least 4-SDs away from the current mean, i.e. $|Q^*R_i - Mean_{i-1}| \geq 4 \times SD_{i-1}$, then this beat is considered as an ectopic beat.

Although 4 SDs has been empirically determined to differentiate an ectopic beat from a normal beat, other multiples of SD may be found to work as well.

If a current beat is recognized as an ectopic beat then its Q*R value is excluded from use in updating the averaging process and the ectopic beat data (i.e. Q*R value and the time of occurrence) is stored in the RAM memory (block 70). If a current beat is a paced beat rather than an intrinsic beat, it too is excluded from the averaging process and computation of SD. Thus, the mean Q*R interval values are contributions only from intrinsic beats with similar Q*R interval values.

The Q*R interval not only can be used to detect ectopic beats, but it also contains information about the location (origination place) of the ectopic beats. The fiducial point Q* can be considered as the time of earliest ventricular excitation. The other point, R, reflects the time when the ventricular depolarization wavefront passes through the sensing electrode 28. Thus the Q*R interval reflects the time required for the electrical excitation wavefront to travel from its origin in the ventricle to the sensing electrode 28. When the conduction velocity is assumed constant within the ventricle, then the Q*R interval also reflects the distance that a ventricular excitation wavefront travels from its origin to the tip of sensing electrode 28. Since the location of the electrode is fixed in a given patient, change in the Q*R interval would mean change in the origin of the electrical excitation. This is the underlying rationale why Q*R interval can be used to detect ventricular ectopic beats which occur in a locus other than the location of the AV node in normal situation. It can be expected that the longer the Q*R interval is compared to the normal value, the farther the ectopic origin is away from the sensing electrode 28. Thus, when the electrode 28 is placed on the left ventricle 31, then a much shorter Q*R interval suggests that the ectopic beat originated in the left ventricle 31, whereas a much longer Q*R interval suggests that the ectopic origin may be in the right ventricle 30.

In some cases, more than one electrode can be placed in the ventricle(s) (i.e., one electrode 27 and 28 in or on each ventricle or two electrodes 28 and 29 in or on the same ventricle. In this multi-electrode configuration, Q*R intervals simultaneously recorded from multiple electrodes can be combined to provide more precise information on the location of an ectopic foci. The time of occurrence of the ectopic beats as sensed from each electrode 27, 28, 29 can be separately stored in ectopic beat memory 70 for later readout and analysis, via telemetry circuit 37 (FIG. 1).

In accordance with a further aspect of the invention, ectopic beats can be grouped based on their Q*R time intervals recorded from all the electrodes 27, 28, 29. Ectopic beats with similar Q*R time intervals are grouped together. Different groups represented by blocks 71, 72, and 73 in FIG. 2 represent different origins of ectopic excitation. The incidence and time of occurrence of each ectopic beat is thus stored according to its group. Then, the distribution of ectopic origins can be obtained from a frequency analysis. Such information may have diagnostic importance, as it may reveal whether a particular ventricular region is abnormally active, which may be indicative of possible pathological change in the substrate in that region. Knowing the precise location of ectopic foci makes it easier to treat the condition through ablation.

The method for detecting ectopic beats as described herein is for ventricular ectopic beats but the method may be applied to ectopic beats anywhere.

When an ectopic beat is detected, the pacing device 10 which may have anti-tachy pacing capabilities known in the art, can switch to an appropriate operating mode best suited to handle tachycardia episodes. The microprocessor 32 then directs the variable frequency pulse generator 38 to send a cardiac stimulating or paced signal over lead 40 to cardiac stimulating electrode 42 to stimulate the heart to beat in a desired manner. The pacing device 10 will then reestablish normal pacing sequence once normal sinus rhythm is detected.

For non-invasive diagnosis of ectopic beats during a physical examination using ECG equipment, electrodes are placed on the chest of the patient, and substantially the same method of measuring the Q*R time interval may be applied.

Obviously, many modifications and variations of the present invention are possible in light of the above teachings. It is therefore to be understood that, within the scope of the appended claims, the invention may be practiced otherwise than as specifically described.

What is claimed is:

1. Apparatus for detecting ectopic beats in a heart of a patient comprising:
   (a) a sensor coupled to the patient that detects ventricular depolarization signals including successive QRS complexes;
   (b) an electronic circuit responsive to an output of the sensor for determining on a beat-to-beat basis, a time interval, T, corresponding to a QR interval of the QRS complex;
   (c) a threshold establishing device operative to process sampled values of the interval, T, over a predetermined plurality of heartbeat cycles to develop a threshold value; and
   (d) a comparator for comparing the T value of a current beat to the threshold value and for signaling the occurrence of an ectopic beat based upon result of the comparison.

2. The apparatus of claim 1 wherein the means for developing a threshold establishing device comprises:
   (a) a computer programmed to dynamically calculate an average length of said time interval, T, over said predetermined plurality of heart beat cycles and a predetermined multiple of a standard deviation of said time interval, T, over said plurality of heartbeat cycles.

3. Apparatus for detecting ectopic beats in a heart of a patient, comprising:
   (a) means for sensing ventricular depolarization signals including successive QRS complexes;
   (b) means responsive to the sensing means for determining, on a beat-to-beat basis, a time interval, T, between a point, Q*, on the QRS complex where an absolute slope reaches a predetermined percentage of a maximum absolute slope of the QRS complex prior to maximum peak slope of the QRS complex and the largest peak of the QRS complex, R;
   (c) means for dynamically calculating an average length of said time interval, T, over a plurality of heartbeat cycles, and a standard deviation of said time interval over said plurality of heartbeat cycles; and
   (d) means for comparing a Q*R interval for a current beat with a predetermined multiple of the standard deviation of said time interval over said plurality of heartbeats to identify whether the current beat is an ectopic beat.

4. The apparatus as in claim 3 wherein the means for comparing determines whether the Q*R interval for a current beat is at least four of said standard deviations.

5. The apparatus of claim 4 and further including memory means for storing a time of occurrence where the Q*R interval for a current beat is at least four of said standard deviations.

6. The apparatus as in claim 3 wherein the means for sensing comprises at least one electrode operatively coupled to the heart of the patient.

7. The apparatus as in claim 6 wherein the at least one electrode is disposed on the left ventricle of the heart.

8. The apparatus as in claim 6 wherein the at least one electrode is disposed within the right ventricle of the heart.

9. The apparatus as in claim 6 wherein the at least one electrode is disposed on the chest of a patient.

10. The apparatus of claim 3 wherein the means responsive to the sensing means comprises:
    means for converting the ventricular depolarization signals to a digital data representative thereof; and
    a microprocessor programmed to perform signal processing on the digital data and to compute the Q* point and an R value and a time interval between the Q* points and the R value for each of a plurality of sequential heartbeats.

11. The apparatus of claim 10 wherein the microprocessor is programmed to dynamically calculate the average length of said time interval, T, over a plurality of heartbeat cycles and the standard deviation of the time interval over said plurality of heartbeat cycles and to compare the Q*R interval for a current beat with a predetermined multiple of the standard deviation of said time interval over said plurality of heartbeats.

12. Apparatus for detecting ectopic beats in a heart of a patient comprising:
    (a) an implantable cardiac rhythm management device having a microprocessor coupled in controlling relation to a stimulating pulse generator, said microprocessor adapted to receive electrogram data from at least one sensing electrode disposed in or on the heart, the microprocessor programmed to compute a time interval, T, between a first detected cardiac event in the electrogram data and a second detected cardiac event in the electrogram data on a beat-to-beat basis and a mean value and a standard deviation of T over a predetermined number of intrinsic beats, the microprocessor further programmed to compare the interval T of a current intrinsic heartbeat to a predetermined multiple of the computed standard deviation; and (b) a memory coupled to the microprocessor adapted to store information identifying an occurrence of an ectopic beat when the interval T of the current intrinsic beat equals or exceeds the predetermined multiple of the standard deviation.

13. The apparatus of claim 12 and further including an electrical lead having an electrode for picking up said electrogram data, and a conductor connecting the electrode to the implantable cardiac rhythm management device.

14. The apparatus of claim 12 and further including an analog-to-digital converter coupled to receive the electrogram data from the sensing electrode and provide a digital representation thereof to the microprocessor.

15. Apparatus for detecting ectopic beats in the heart comprising:

a sensor for detecting electrical activity in the heart, a lead for transmitting electrical signals from the sensor, an amplifier connected to the lead for amplifying the electrical activity signals detected by the sensor, an analog to digital converter connected to the amplifier to change the analog signal to a digital signal, and a microprocessor with a memory for storing the digital signal data and programmed for calculating a Q*R interval for each beat, the mean Q*R interval and the standard deviation of the mean Q*R interval and comparing the Q*R interval of a beat to a predetermined multiple of the standard deviation to determine an ectopic beat has occurred.

16. Apparatus for detecting ectopic beats in the heart as in claim 15 and further having:

a transmitter for sending data from the microprocessor to a receiver for recording and displaying data acquired from the heart.

17. Apparatus for detecting ectopic beats in the heart as in claim 15 and further having:

a variable frequency pulse generator connected to the microprocessor for generating pulses to be sent to the heart at the microprocessor's command, a lead from the pulse generator to the heart for carrying the pulse to the heart, and an electrode coupled to the heart for receiving the pulse and stimulating the heart.

18. A method for detecting ectopic beats in a heart comprising:

detecting electrical activity in the heart on a beat-to-beat basis to obtain Q–R interval values, computing a mean Q–R interval and its standard deviation over a predetermined number of normal heartbeats, and comparing the Q–R interval of a current heartbeat to determine whether it is greater than a predetermined number of standard deviations of the mean Q–R interval for determining if an ectopic beat has occurred.

19. A method for detecting ectopic beats in a heart as in claim 18 further comprising:

sensing electrical events in the heart from one sensor to provide the onset of the QRS complex and a peak value R for determining the QR interval of each beat.

20. A method for detecting ectopic beats in a heart as in claim 19 further comprising:

placing the sensor on the left ventricular endocardium.

21. A method for detecting ectopic beats in a heart as in claim 19 further comprising:

placing the sensor on the left ventricular epicardium.

22. A method for detecting ectopic beats in a heart as in claim 19 further comprising:

placing the sensor in the right ventricle.

23. A method for detecting ectopic beats in a heart as in claim 19 further comprising:

placing the sensor on a patient's chest.

24. A method for detecting ectopic beats in a heart as in claim 18 further comprising:

detecting electrical activity in the heart from more than one sensor to provide data for determining an ectopic focus.

25. A method for detecting ectopic beats in a heart as in claim 24 further comprising:

storing times of occurrence of detected ectopic beats in groups to assess the frequency and place of origin of ectopic beats.

26. A method for detecting ectopic beats in a heart as in claim 18 further comprising:

transmitting QR interval data, mean QR interval data and mean standard deviation of QR interval data to a device for recording and displaying the data to a health care provider for monitoring and diagnosis of patients.

27. A method for detecting ectopic beats in a heart as in claim 18 and further including the steps of:

dynamically smoothing electric signals representative of the ECG waveform using a weighted N-point moving window; and where R defined as the largest peak in a smoothed QRS complex; and the onset of the QRS complex as a Q* data point is measured as the earliest point on the smoothed QRS complex where the slope of the QRS wave is a predetermined percentage of the maximum slope of the QRS complex prior to the R data point.

28. A method for detecting ectopic beats in a heart as in claim 18 wherein:

computing the mean and standard deviation of the time interval between the Q and R data point comprises the steps of solving the following equations wherein normal intrinsic beats only are used:

$$Mean_i = k1 \times Mean_{i-1} + k2 \times QR_i$$

$$MSE_i = k1 MSE_{i-1} + k2(QR_i - Mean_i)^2$$

$$SD_i = \sqrt{MSE_i}$$

where $Mean_{1-1}$ and $MSE_{i-1}$ are the mean and mean square error for an immediately preceding beat; $QR_i$ is a QR interval value for a current beat; $Mean_i$, $MSE_i$ and $SD_i$ are the updated mean, mean square error, and standard deviation; k1, k2 are weighting coefficients wherein, k1=(M−1)/M, and k2=1/M, where M is the number of normal beats from which the initial Mean and SD had been calculated.

29. Apparatus for detecting ectopic beats in a heart of a patient comprising:

(a) an implantable cardiac rhythm management device having a microprocessor coupled in controlling relation to a stimulating pulse generator, said microprocessor adapted to receive electrogram data from at least one sensing electrode disposed in or on the heart, the microprocessor programmed to compute a time interval, T, between a first detected cardiac event in the electrogram data and a second detected cardiac event in the electrogram data on a beat-to-beat basis and a mean value and a standard deviation of T over a predetermined number of intrinsic beats, the microprocessor further programmed to compare the interval T of a current intrinsic heartbeat to a valve equal to four times the computed standard deviation; and (b) a memory coupled to the microprocessor adapted to store information identifying an occurrence of an ectopic beat when the interval T of the current intrinsic beat equals or exceeds the predetermined multiple of the standard deviation.

30. Apparatus for detecting ectopic beats in a heart of a patient comprising:

(a) an implantable cardiac rhythm management device having a microprocessor coupled in controlling relation to a stimulating pulse generator, said microprocessor adapted to receive electrogram data from at least one sensing electrode disposed in or on the heart, the microprocessor programmed to compute a time interval, T, between a first detected cardiac event in the electrogram data and a second detected cardiac event in the electrogram data on a beat-to-beat basis and a mean value and a standard deviation of T over a predetermined number of intrinsic beats, the microprocessor further programmed to compare the interval T of a current intrinsic heartbeat to a predetermined multiple of the computed standard deviation, (b) a memory coupled to the microprocessor adapted to store information identifying an occurrence of an ectopic beat when the interval T of the current intrinsic beat equals or exceeds the predetermined multiple of the standard deviation; and (c) an analog-to-digital converter coupled to receive the electrogram data from the sensing electrode and to provide a digital representation thereof to the microprocessor, the microprocessor being programmed to provide dynamic smoothing to the digital representation of the electrogram data.

* * * * *